United States Patent [19]
Taicher et al.

[11] Patent Number: 5,828,214
[45] Date of Patent: Oct. 27, 1998

[54] METHOD AND APPARATUS FOR RESISTIVITY DETERMINATION BY NUCLEAR MAGNETIC RESONANCE MEASUREMENT

[75] Inventors: Gersh Z. Taicher; Arcady Reiderman, both of Rehovot, Israel

[73] Assignee: Western Atlas International, Inc., Houston, Tex.

[21] Appl. No.: 625,211

[22] Filed: Apr. 1, 1996

Related U.S. Application Data

[63] Continuation-in-part of Ser. No. 606,089, Feb. 23, 1996.

[51] Int. Cl.$^6$ ........................................... G01V 3/14
[52] U.S. Cl. .................................................. 324/303
[58] Field of Search ........................ 324/300, 303, 324/307, 309, 318, 322, 338–341

[56] References Cited

U.S. PATENT DOCUMENTS

| | | | |
|---|---|---|---|
| 3,617,867 | 11/1971 | Herzog | 324/303 |
| 4,769,602 | 9/1988 | Vinegar et al. | 324/307 |
| 5,278,501 | 1/1994 | Guilfoyle | 324/303 |
| 5,432,446 | 7/1995 | MacInnis et al. | 324/303 |
| 5,557,200 | 9/1996 | Coates | 324/303 |

OTHER PUBLICATIONS

E.L. Bigelow, "Introduction to Wireline Log Analysis", Western Atlas Logging Services, Houston, Texas 1992, pp. 123–124.

E. Bigelow, "Introduction to Wireline Log Analysis" Western Atlas Logging Services, Houston, TX 1992, pp. 55–71.

*Primary Examiner*—Sandra L. O'Shea
*Assistant Examiner*—Roger C. Phillips
*Attorney, Agent, or Firm*—Richard A. Fagin

[57] ABSTRACT

An apparatus for measuring conductivity of earth formations penetrated by a wellbore including a magnet for inducing a static magnetic field in the earth formations penetrated by the wellbore. The apparatus includes means for generating a radio frequency magnetic field in the wellbore and the earth formations, means for selectively varying a frequency of the radio frequency magnetic field, and means for receiving a nuclear magnetic resonance signal from excited nuclei in the earth formations. The means for receiving includes means for measuring a difference in phase between the magnetic resonance signal and the radio frequency magnetic field. The phase difference measured is related to the conductivity of the earth formations.

58 Claims, 5 Drawing Sheets

METHOD AND APPARATUS FOR RESISTIVITY DETERMINATION BY NUCLEAR MAGNETIC RESONANCE MEASUREMENT

CROSS REFERENCE TO RELATED APPLICATIONS

The present application is a continuation-in-part of a patent application filed on Feb. 23, 1996, U.S. Ser. No. 08/606,089, entitled "Nuclear Magnetic Resonance Apparatus and Method".

BACKGROUND OF THE INVENTION

1. Field of the Invention

The present invention is related to the field of nuclear magnetic resonance (Next) well logging apparatus and methods. More specifically, the present invention is related to apparatus and methods for determining the electrical resistivity of earth formations penetrated by a wellbore by using particular aspects of measurements of nuclear magnetic resonance in the earth formations.

2. Description of the Related Art

Various devices are known in the art for measuring electrical resistivity (or its converse, conductivity) of earth formations penetrated by wellbores. Electrical resistivity measurements are used for, among other things, inferring the fluid content within pore spaces of some of the earth formations.

Devices known in the art for determining electrical resistivity include galvanic devices, such as a "dual laterolog tool" as described in "Introduction to Wireline Log Analysis", Western Atlas International, Inc. Houston, Tex., 1992. In most general terms, galvanic devices inject electrical current into the earth formations and measure, in some form, voltage drop of the injected current across the earth formations to determine their resistivity.

Resistivity measuring devices known in the art also include electromagnetic induction tools. Electromagnetic induction tools are also described in the "Introduction to Wireline Log Analysis" reference, supra. Electromagnetic induction tools typically induce alternating electromagnetic fields in the earth formations, which in turn induce signals in receivers on the instrument. The induced signals correspond to the electrical resistivity of the earth formations.

Both electromagnetic induction tools and galvanic resistivity tools have a common limitation, namely that the signals generated in response to the formation resistivity, in either type tool, are dependent at least to some degree on the resistivity of a fluid which typically fills the wellbore for the purpose of drilling and the extent to which the wellbore fluid has been forced by differential pressure into the pore spaces of the earth formations. The diameter of the wellbore also affects the measurements made by resistivity tools known in the art. It is difficult using resistivity devices known in the art to determine resistivity of, and as a consequence infer the native fluid content of, that portion of the earth formations which remain unaffected by wellbore fluid infiltration into the pore spaces of the formation. The difficulty in determining the resistivity of the part of the formation unaffected by fluid infiltration results precisely because at least some of the response of the resistivity tools known in the art originates from within the wellbore and from within the portion of the earth formations subject to the fluid infiltration. Because the radial depth to which the wellbore fluid penetrates the formations cannot be directly determined, the effect of the fluid infiltration on the overall resistivity measurement is difficult to quantify.

Another drawback to the resistivity tools known in the art is that resistivity measurements are not useful by themselves for determining fluid type and content in the pore spaces of the earth formations. It is usually necessary to determine in addition to the resistivity, the fractional volume of the pore spaces. This generally necessitates using an additional measuring instrument to measure the fractional volume of pore spaces (porosity). Typically these additional instruments do not measure the porosity from within the same portion of the earth formations as do the resistivity measuring devices known in the art. Inferences of fluid content made from resistivity and porosity measurements made from different portions of the earth formations may be subject to error, as the porosity may not be homogeneous within the earth formation. A need exists for a single instrument which can determine both resistivity and porosity from the same portion of the earth formations.

Accordingly, it is an object of the present invention to provide a means for determining resistivity of the earth formation only from a selected radial depth within the formation from the center of the wellbore.

It is a further object of the present invention to provide a means for determining the resistivity of the earth formations at a plurality of selected radial depths within the earth formation so that the depth of penetration of the wellbore fluid, and the resistivity of the non-infiltrated formation, can be more precisely determined.

It is yet another object of the present invention to provide a single instrument which can measure both the resistivity and the porosity of earth formations from the same portion of the earth formation.

SUMMARY OF THE INVENTION

The present invention is an apparatus for measuring the electrical resistivity of earth formations penetrated by a wellbore. The apparatus includes a magnet for inducing a static magnetic field in the earth formations penetrated by the wellbore. The apparatus includes means for generating a radio frequency magnetic field in the wellbore and in the earth formations. The means for generating the radio frequency magnetic field includes means for selectively varying a frequency of the radio frequency magnetic field. The apparatus also includes means for receiving nuclear magnetic resonance signals from excited nuclei in the earth formations. In a preferred embodiment of the invention, the means for generating and means for receiving include a coil wound so that turns of the coil lie in a plane substantially perpendicular to the longitudinal axis. The means for receiving includes means for measuring a difference in phase between the magnetic resonance signal and the radio frequency magnetic field. The phase difference measured is related to the resistivity of the earth formations.

In a preferred embodiment, the coil includes a high magnetic permeability ferrite disposed in the coil, and a selectively controllable means for applying a static magnetic field to the ferrite so as to change the resonant frequency of the coil, and thereby the frequency of the radio frequency magnetic field.

The present invention includes a method for determining the electrical resistivity of a medium, including inducing a static magnetic field in the medium. The method includes generating a radio frequency magnetic field in the medium at a first frequency so as to excite nuclei of the medium, receiving nuclear magnetic resonance signals at the first frequency, generating the radio frequency magnetic field in the medium at a second frequency, receiving the nuclear magnetic resonance signals at the second frequency, measuring a difference in phase, with respect to a predetermined phase reference, between the resonance signal measured at the first frequency and the resonance signal at the second frequency, and calculating the resistivity from the difference in phase.

The present invention also provides a method of determining resistivity and porosity of earth formations from within the same region within the earth formations. The method includes generating a radio frequency magnetic field in the medium at a first frequency so as to excite nuclei of the medium, receiving nuclear magnetic resonance signals at the first frequency, generating the radio frequency magnetic field in the medium at a second frequency, receiving the nuclear magnetic resonance signals at the second frequency, measuring a difference in phase between the resonance signal measured at the first frequency and the resonance signal at the second frequency, and calculating the resistivity from the difference in phase. The porosity of the earth formations is determined by calculating nuclear spin relaxation time from the nuclear magnetic resonance measurements.

DESCRIPTION OF THE PREFERRED EMBODIMENT

1. Description of the Apparatus

Figure 1:
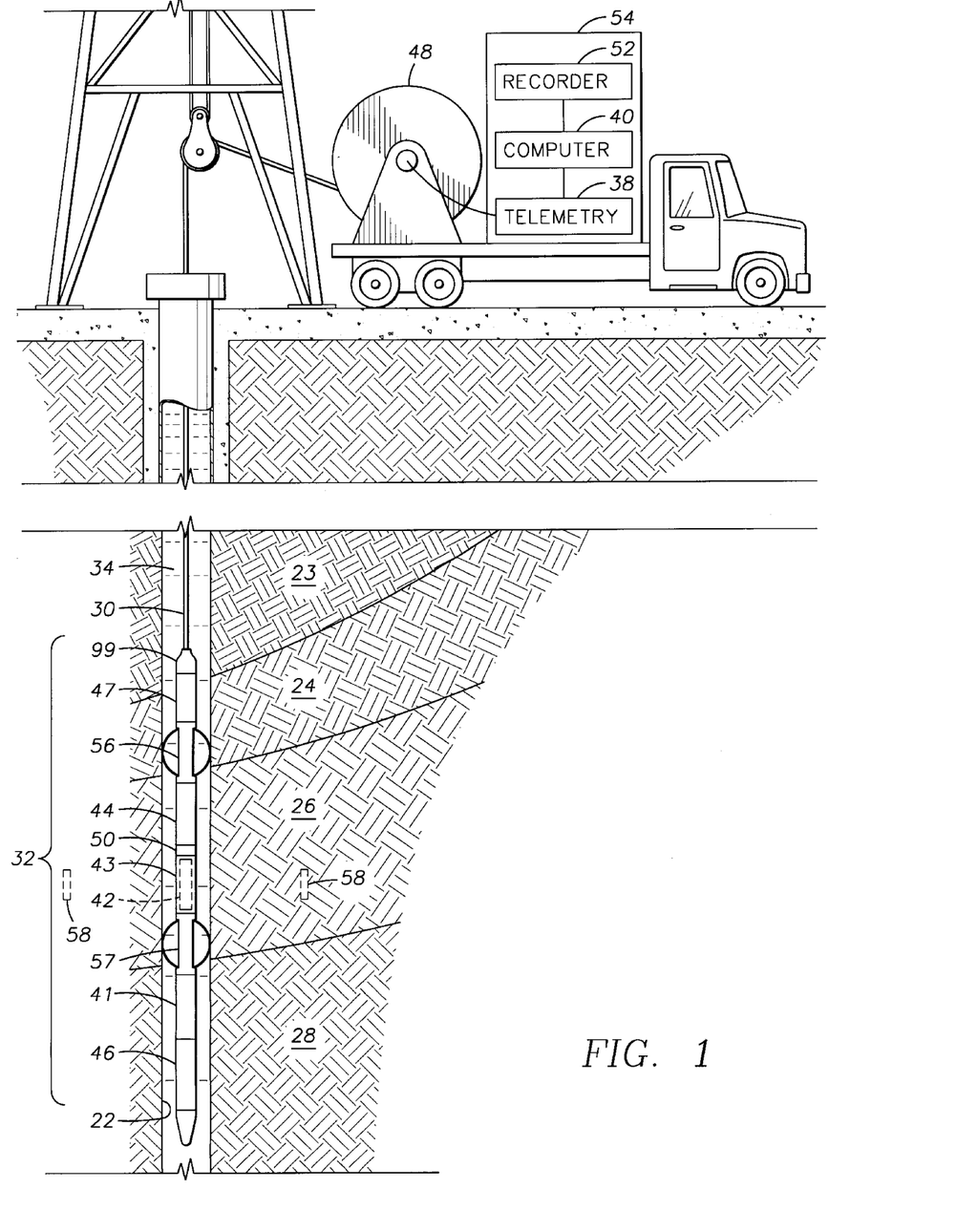
FIG. 1 shows a well logging apparatus as it is typically used in a wellbore penetrating earth formations.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud". A "sensitive volume", shown generally at 5 8 and having generally cylindrical shape, is disposed in one of the earth formations, shown at 26. The sensitive volume 58 is a predetermined portion of the earth formations 26 in which nuclear magnetic resonance (NMR) measurements are made, as will be further explained.

A string of logging tools 32, which can include an NMR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer can also include a data recorder 52 for recording measurements made by the apparatus and transmitted to the surface equipment 54.

An NMR probe 42 according to the present invention can be included in the tool string 32. The tool string 32 is preferably centered within the wellbore 22 by means of a top centralizer 56 and a bottom centralizer 57 attached to the tool string 32 at axially spaced apart locations. The centralizers 56, 57 can be of types known in the art such as bowsprings.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors. The locations of the other sensors 41, 46, 47 shown in FIG. 1 are a matter of convenience for the system designer and are not to be construed as a limitation on the invention.

Figure 2:
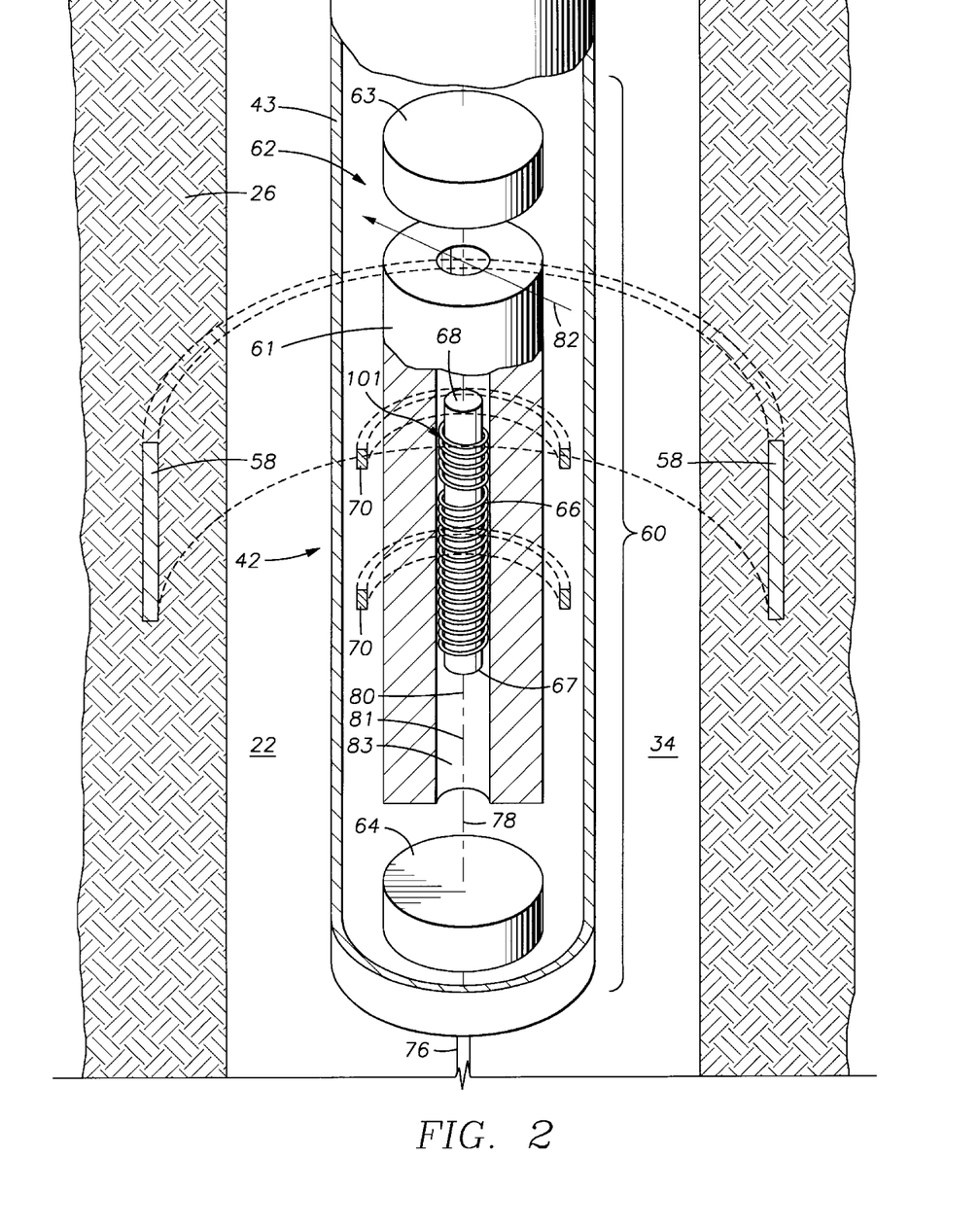
FIG. 2 shows an NMR probe section of the well logging apparatus of FIG. 1 in more detail.

FIG. 2 shows the NMR probe 42 in more detail. The NMR probe 42 preferably comprises a generally cylindrical permanent or electro-magnet assembly 60. The magnet assembly 60 can include at least one permanent magnet 62, which preferably has a substantially circular cross section and is generally elongated along a magnet axis 80. The magnet axis 80 is preferably positioned coaxially with the longitudinal axis 76 of the wellbore (22 in FIG. 1). Alternatively, a plurality of permanent magnets may be used to make the magnet assembly 60. For clarity of the description of the invention, the one or more permanent magnets 62 will be considered together and referred to as permanent magnet 62, and their common axis 80 and the collocated axis of the wellbore (22 in FIG. 1) will be jointly identified herein as the longitudinal axis, shown at 78.

The permanent magnet 62 preferably has substantially uniform magnetization along the longitudinal axis 78. The magnet 62 also preferably has a magnetization direction 82 which is substantially perpendicular to the longitudinal axis 78. The permanent magnet 62 should have an overall length along the longitudinal axis 78 which is greater than twice the dimension of the permanent magnet 62 perpendicular to the longitudinal axis 78. The overall length of the permanent magnet 62 should also generally be greater than twice the diameter of the sensitive volume 58 as will be further explained.

The permanent magnet 62 preferably comprises a main permanent magnet 61, a top end magnet 63 located above the main permanent magnet 61 and a bottom end magnet 64 located below the main permanent magnet 61. The end magnets 63, 64 are provided to reduce axial asymmetry of the static magnetic field generated by the permanent magnet 62 in the sensitive volume 58.

The main permanent magnet 61 is preferably formed into an annular cylinder having a hole 83 of substantially circular cross section. The axis 81 of the magnet hole 83 is preferably parallel to the longitudinal axis 78. Details of the static magnetic field imparted by the permanent magnet 62 within the sensitive volume 58 and within the magnet hole 83 will be further explained. It is to be understood that the cylindrical shape of the permanent magnet 62 and the hole 83 are preferred but not essential. An essential feature of the magnet 62 is that the direction of the static magnetic field induced by the magnet 62 be substantially perpendicular to the longitudinal axis 78. If the shape of the magnet 62 is other than cylindrical, for example, elliptical, the hole 83 should have the same general shape and the same ratio of long axis to short axis as the magnet 62 in order that the static magnetic field inside the hole 83 be substantially equal to zero, as will be further explained.

The main permanent magnet 61 can be made from a ferrite magnet material such as that sold under the trade name "Spinalor" and manufactured by Ugimag, 405 Elm St., Valparaiso, Ind., or another material sold under the trade name "Permadure" and manufactured by Philips, 230 Duffy Ave., Nicksville, N.Y. The permanent magnet material of the main permanent magnet 61 should be electrically non-conductive, so that an antenna used to generate a radio frequency magnetic field can be located in the hole 83, as will be further explained.

The top end magnet 63 and the bottom end magnet 64 may be formed from the same or similar ferrite permanent magnet material as is the main permanent magnet 61. Alternatively, the end magnets 63, 64 may be formed form magnetically stronger material such as a neodymium-iron-boron magnet alloy sold under the trade name "Ugistab" and manufactured by Ugimag, 405 Elm St., Valparaiso, Ind., or another material sold under trade name "Vacodym" and manufactured by Vacuumschmelze GMBH, 9/7 Rhenaniastrasse St., Berlin, Germany. Alternatively, the top end magnet 63 and the bottom end magnet 64 may be formed from samarium-cobalt permanent magnet material such as one sold under trade name "Recoma" and manufactured by Ugimag, 405 Elm St., Valparaiso, Ind., or another sold under trade name "EEC" and manufactured by Electron Energy Corp., 924 Links Ave., Landsville, Pa. The material forming the top end magnet 63 and the bottom end magnet 64 need not be electrically non-conductive.

The NMR probe 42 further includes the previously described transceiver antenna 67, which can comprise one or more coil windings 66 preferably arranged inside the hole 83 in the main permanent magnet 61. The coil windings 66 are preferably arranged so that each coil winding 66 lies substantially in a plane perpendicular to the longitudinal axis 78. Radio frequency (RF) alternating current passing through the coil windings 66 generates an RF magnetic field in the earth formation 26 in FIG. 1). The RF magnetic field generated by the current flow in the coil windings 66 has field directions substantially parallel to the longitudinal axis 78 within the sensitive volume 58.

The coil windings 66 have should have an overall length parallel to the longitudinal axis 78 which is about equal to the diameter of the sensitive volume 58. The overall length of the coil windings 66 parallel to the longitudinal axis 78 should also be substantially shorter than the overall length of the main permanent magnet 62 along the longitudinal axis 78, as will be further explained.

Preferably, the coil windings 66 are formed around a soft ferrite rod 68. The soft ferrite rod 68 can be formed from material such as that sold under trade designation "F6" and manufactured by MMG-North America, 126 Pennsylvania Ave., Paterson, N.J., or another sold under trade designation "3C2" and manufactured by Philips, 230 Duffy Ave., Nicksville, N.Y. The ferrite rod 68 preferably is located coaxially with the longitudinal axis 78. The overall length of the ferrite rod 68 along the longitudinal axis 78 should be substantially less than the length of the permanent magnet 62 along the longitudinal axis 78. Alternatively, a plurality of coils and a plurality of ferrite rods may be employed. The assembly of coil windings 66 and soft ferrite rod 68 will be referred to hereinafter as the transceiver antenna 67. The ferrite rod 68 has the particular function of increasing the field strength of the RF magnetic field generated by the transceiver antenna 67. Using the ferrite rod 68 particularly enables the transceiver antenna 67 to have a relatively small external diameter so that it can be located in the hole 83. Having a small external diameter particularly enables the transceiver antenna 67 of the present invention to be sized so that the apparatus of the present invention can be used in smaller diameter wellbores.

The transceiver antenna 67 also can include a frequency control coil 101, which can be another wire coil wound around the ferrite rod 68. As will be further explained, a control voltage selectable by the system operator can be applied to the frequency control coil 101 to tune the transceiver antenna 67 when the frequency of the RF source 93 is changed. The purpose of changing the frequency, and the source of the control voltage will be further explained.

The NMR probe 42, can also comprise one or more additional receiver coils, such as the one shown generally at 70 (only the lead-in wires are shown in FIG. 2 for clarity) which are arranged about the exterior surface of the permanent magnet 62. Each turn (not shown in FIG. 2) of additional receiver coil 70 should lie in a plane substantially parallel to a plane containing both the magnetization axis 82 of the permanent magnet 62 and containing the longitudinal axis 78. Preferably the additional receiver coil 70 has an overall length parallel to the longitudinal axis 78 which is less than the overall length of the transceiver antenna 67. As a consequence, the overall length of the additional receiver coil 70 parallel to the longitudinal axis 78 should be substantially shorter than the length of the permanent magnet 62 along the longitudinal axis 78. Alternatively, a plurality of additional receiver coils 70 may be included in the NMR probe 42. A particular property of the additional receiver coil 70 arranged as described herein is that it is substantially orthogonal to, and consequently substantially insensitive to, the direct RF magnetic field generated by the transceiver antenna 67. This insensitivity to the direct RF field enables the additional receiver coil 70 to provide the apparatus of the present invention with very short "dead time", while the current flowing through the transceiver antenna 67 decays to zero.

The permanent magnet 62, the transceiver antenna 67 and the additional receiver coil 70 are preferably housed within a non-conductive, non-ferromagnetic protective housing 43. Such housings and additional components (not shown) for excluding the drilling mud under high hydrostatic pressure, are familiar to those skilled in the art.

Figure 3:
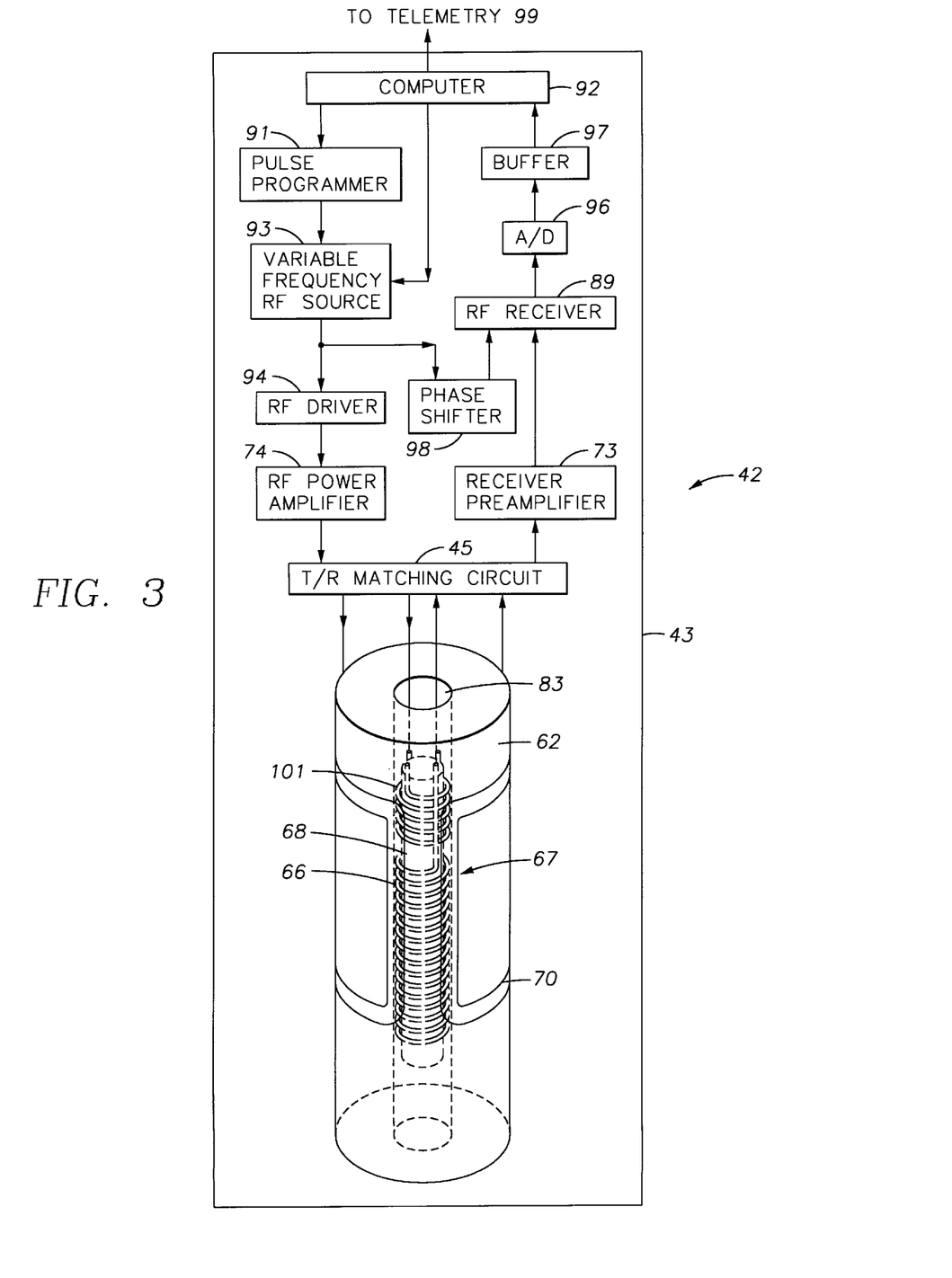
FIG. 3 shows functional block diagram of the NMR probe of FIG. 2.

FIG. 3 shows, in general form, the NMR probe 42 and a functional block diagram of the NMR well logging apparatus according to the present invention. A transmitter/receiver (T/R) matching circuit 45 can be disposed within the housing 43. The T/R matching circuit 45 typically includes a series of resonance capacitors (not shown separately), a transmitter/receiver switch (not shown separately) and both "to-transmitter" and "to-receiver" matching circuitry. The T/R matching circuit 45 can be coupled both to a radio frequency (RF) power amplifier 74 and to a receiver preamplifier 73. While shown as located inside the housing 43 the T/R matching circuit 45, the RF power amplifier 74 and the receiver preamplifier 73 may alternatively be located outside the housing 43 within the top centralizer (56 in FIG. 1) or within the NMR electronics cartridge (44 in FIG. 1). The locations of the T/R matching circuit 45, the RF power amplifier 74 and the receiver preamplifier 73 are not to be construed as a limitation on the invention.

Part of the control circuitry for the NMR logging apparatus includes a downhole computer 92, which among other functions provides control signals to a pulse programmer 91. The computer 92 and the pulse programmer 91 may also be located within the top centralizer 56 or in the NMR electronics cartridge 44. The pulse programmer 91 receives an RF signal input from a variable frequency RF signal source 93. The pulse programmer 91 controls the timing and operation of both the variable frequency RF signal source 93 and an RF driver 94. The RF driver 94 receives an input from the variable frequency RF source 93 and provides an output to the RF power amplifier 74. The RF power amplifier 74 provides a high power signal to drive the transceiver antenna 67 for generating an RF magnetic field in the sensitive volume (58 in FIG. 1). The RF power amplifier 74 can be electrically connected (typically by the switch in the T/R matching circuit 45) to the transceiver antenna 67 during transmission of RF power pulses.

During reception of the induced NMR signal, the transceiver antenna 67 and/or the additional receiver antenna 70 can be electrically connected to the receiver preamplifier 73. The output of the RF receiver preamplifier 73 is provided to an RF receiver 89. The RF receiver 89 also receives a phase reference input from a phase shifter 98. The phase shifter 98 receives a primary phase reference input from the variable frequency RF source 93. The RF receiver 89 provides an output to an A/D converter 96. The A/D converter 96 output can be stored in a buffer 97 until required for use by the down-hole computer 92. Alternatively, the buffer 97 contents can be conducted directly to a downhole part of the telemetry unit 99 for transmission to the surface equipment (54 in FIG. 1).

The downhole computer 92 typically preprocesses the data from the buffer 97 and transfers the preprocessed data to the downhole portion of the telemetry system, shown generally at 99. The downhole portion of the telemetry system 99 transmits the preprocessed data to the telemetry unit (38 in FIG. 1) in the surface equipment (54 in FIG. 1). The telemetry unit 38 transfers the data to the surface computer (40 in FIG. 1) for calculating and presenting desired well logging output data for further use and analysis as is understood by those skilled in the art.

All of the elements described herein and as shown in FIG. 3, except the transceiver antenna 67, the magnet assembly (60 in FIG. 2) and the additional receiver antenna 70, at the convenience of the system designer may be disposed within the housing 43, the top centralizer (56 in FIG. 1) or the NMR electronics cartridge (44 in FIG. 1). These same elements may alternatively be located at the earth's surface, for example in the surface equipment 54 using the cable (30 in FIG. 1) for transmission of electrical power and signals to the transceiver antenna 67 and the additional receiver antenna 70.

2. Description of the Theory of Operation

The means by which the present invention can be used to determine resistivity of the earth formations (such as 26 in FIG. 1 will now be explained. The magnet 62 generates a static magnetic field having a well defined amplitude gradient, meaning that the static magnetic field amplitude decreases with respect to radial distance from the longitudinal axis 78 in a known manner. A nuclear magnetic resonance condition is generated in the sensitive volume 58 where the frequency of the RF magnetic field matches a nuclear spin precession frequency for the nuclei in the earth formation. The spin precession frequency is dependent on the amplitude of the static magnetic field and on a scale factor (constant) which is unique to each chemical elemental isotope, this constant being called the gyromagnetic ratio ($\gamma_0$). The radius of the sensitive volume 58 can therefore be changed by selecting the frequency of the RF magnetic field when a static magnetic field having an amplitude gradient, such as induced by the permanent magnet 62 in the present invention is used. In the present invention, as previously explained, the frequency of the RF magnetic field can be changed by adjusting the frequency of the RF source 93. The tuning of the transceiver antenna 67 can be adjusted to match the RF source 93 frequency by applying a DC voltage to the frequency control coil 101. When the DC voltage is passed through the frequency control coil 101, the ferrite rod 68 becomes partially magnetized, changing its magnetic permeability. When the magnetic permeability of the ferrite rod 68 is changed, the transceiver antenna 67 can be easily tuned to the new frequency.

The DC voltage which is applied to the frequency control coil 101 can be supplied by any one of a wide variety of circuits known to those skilled in the art. The magnitude of the DC voltage can be directly controlled by the system operator or can be controlled by the down hole computer 92. The type of DC source and the manner of controlling its output magnitude are not meant to limit the present invention.

If the amplitude gradient of the static magnetic field is steep enough, the sensitive volume 58 comprises a thin annular cylinder, the thickness of which depends on the bandwidth of the receiver 89 and the amplitude gradient at the radius of the sensitive volume 58 for the particular RF magnetic field frequency selected. Irrespective of the actual thickness of the annular cylinder which forms the sensitive volume 58, since a resonance condition is generated only in the sensitive volume 5 8, substantially no signal to which the receiver 89 is sensitive originates in any other region around the wellbore (2 in FIG. 1). Further, the radius of a particular sensitive volume associated with each selected RF magnetic field frequency can be accurately determined.

As is known in the art, when electromagnetic energy is propagated as a plane wave through a homogeneous conductive medium, the magnetic vector (analogous to the electric vector, see for example, "Classical Electricity and Magnetism", W. K. H. Panofsky, M. Phillips, Addison-Wesley Publishing Co., Inc., 1962, p. 201) can be described by the following expression:

$$H = H_0 e^{r(\sqrt{\mu_0 \omega \sigma /2})} e^{i(\sqrt{\mu_0 \omega \sigma /2} - \omega t)} \quad (1)$$

where H represents the magnetic vector, $H_0$ represents the magnetic vector at the source of the electromagnetic energy, $\omega$ represents the frequency of the electromagnetic energy, $\sigma$ represents the conductivity of the medium and r represents the distance from the source. As can be determined from the expression in equation (1), the amplitude and phase of H depend on distance from the source and conductivity (or resistivity) of the medium. In the NMR instrument of FIG. 2, the electromagnetic energy (the RF magnetic field generated by the transceiver antenna 67 and received therein or by the additional receiver antenna 70) propagates through the medium, such as the earth formations (26 in FIG. 1), twice, once when transmitted and once again as nuclear magnetic resonance signals are received from the sensitive volume (58 in FIG. 1). The phase of the electromagnetic energy is changed with respect to the phase of the energy at the source from which the energy originates.

The amount of the phase change can be related to the conductivity of the medium and the distance through which the wave travels in the conductive medium by the expression:

$$\phi = (\sqrt{\mu_0 \omega \sigma / 2}) \cdot r \quad (2)$$

where $\mu_0$ represents the magnetic permeability of the medium, $\omega$ represents the frequency of the electromagnetic energy, and $\sigma$ represents the electrical conductivity of the medium. r represents radius within the earth formation (26 in FIG. 1) at which the phase (and consequently the conductivity) is to be determined.

The phase change which takes place between the transmission of the electromagnetic energy and the reception of the magnetic resonance signal at any particular radius from the point of transmission is related to the conductivity of every part of the media surrounding the point of transmission. For the NMR probe 42 of the present invention, the media include the fluid (34 in FIG. 1) in the wellbore (2 in FIG. 1), and any portion of the earth formations 26 which may have the fluid 34 forced into its pore spaces by differential pressure, these portions being known in the art as "invaded zones". It is possible, by measuring phase shift at two different RF magnetic field frequencies, to determine the conductivity only within an annular space between the sensitive volume defined by the radius of the first frequency and a second sensitive volume defined by the radius of the second frequency. If the conductivity $\sigma$ is assumed first to be a slowly changing function with respect to r, the total phase shift can be estimated by the following expression:

$$\phi(R) = 2 \int_{R_t}^{R} (\sqrt{\mu_0 \omega_2 \sigma(r)/2}) dr \quad (3)$$

where $R_t$ represents the radius of the antenna (such as transceiver antenna 67 in FIG. 2), and R represents the radius of the sensitive volume 58. R is typically a known function of $\omega$ because the magnet (62 in FIG. 2) induces a static magnetic field ($B_0(R)$) having known radial dependence. For example, if the static magnetic field ($B_0(R)$) is defined radially by $B_0(R) = \alpha/R^2$ where $\alpha$ represents a constant of proportionality, then from an expression for the resonance condition $\gamma B_0(R) = \omega$, the radial dependence of the sensitive volume can be expressed as:

$$R(\omega) = \sqrt{(\alpha \gamma / \omega)} \quad (4)$$

If the phase is measured at frequency $\omega$ and is again measured at a second incrementally changed frequency ($\omega + \Delta \omega$), the phase shift at the second frequency can be estimated by the expression:

$$\phi(\omega + \Delta \omega) \approx \phi(\omega) + \left( \frac{\partial \phi}{\partial \omega} \right) \cdot \Delta \omega \quad (5)$$

By substituting into equation (2), an expression for the phase shift at radius R can be shown as:

$$\phi(\omega + \Delta \omega) \approx \phi(\omega) + \left( \frac{-\phi}{2\omega} + \sqrt{\frac{\mu_0 \omega \sigma(R)}{2}} \right) \cdot \left( \frac{\partial R}{\partial \omega} \right) \cdot \Delta \omega \quad (6)$$

wherein $\sigma(R)$ represents the conductivity of at radius R. Solving equation (6) for the conductivity $\sigma(R)$ yields the following expression:

$$\sigma[R(\omega)] \approx \left[ \frac{\phi(\omega + \Delta \omega) - \phi(\omega)}{\Delta \omega} + \frac{\phi}{2\omega} \right]^2 \cdot \left[ \sqrt{\frac{\mu_0 \omega}{2}} \left( \frac{\partial R}{\partial \omega} \right) \right]^{-2} \quad (7)$$

The phase of the electromagnetic energy which is detected by the antenna (such as 67 or 70 in FIG. 2) can be determined by sampling the output of the phase shifter (98 in FIG. 3) and transmitting the value determined therein to the computer (92 in FIG. 3) for inclusion in the data signals transmitted to the surface equipment (54 in FIG. 1). Other methods of determining the phase of the signals detected in the antenna are known in the art. The means for measuring phase described herein is not meant to limit the invention. It is also to be understood that measuring the phase as described herein, by sampling the output of the phase shifter, is not meant to limit the phase reference with respect to which the phase of the detected NMR signal is determined. It is contemplated any predetermined phase reference can be used to determine the amount of phase shift in the NMR signal caused by the conductivity of the media surrounding the instrument.

A particular advantage of the present invention is that it can be used to make resistivity measurements responsive in different directions with respect to the earth formation. For example, when the RF power pulses are applied to the transceiver antenna (67 in FIG. 2), the electric field which is thereby induced in the formation as a result of the RF magnetic field is substantially perpendicular to the longitudinal axis (78 in FIG. 2). Resistivity measurements made using the transceiver antenna 67 therefore substantially correspond to the formation resistivity perpendicular to the axis of the wellbore (2 in FIG. 1). It can be readily inferred that resistivity measurements can also be made using RF power pulses conducted through the additional receiver (70 in FIG. 2). Resistivity measurements made using the additional receiver 70 would substantially correspond to the formation resistivity parallel to the axis of the wellbore 2. Resistivity measurements made in both directions as described herein in the same earth formation can provide an indication of the electrical anisotropy of that particular earth formation.

Another particular advantage of the present invention is that it makes possible measurements of resistivity segregated by radial depth in the formation. By making nuclear magnetic resonance measurements at a plurality of pairs of sensitive volumes, and determining the phase shifts therebetween (and consequently determining the conductivities of the earth formation therebetween), it is also possible using the present invention to generate a "map" of the conductivity of the earth formation with respect to the radial distance from the wellbore 2.

DESCRIPTION OF ALTERNATIVE EMBODIMENTS

Figure 4A:
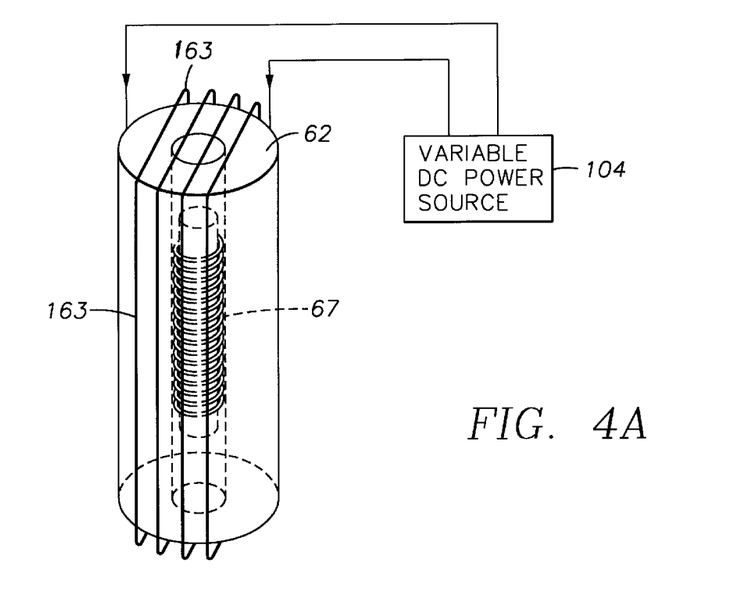
FIG. 4A shows an alternative embodiment of the NMR probe of FIG. 2.
Figure 4B:
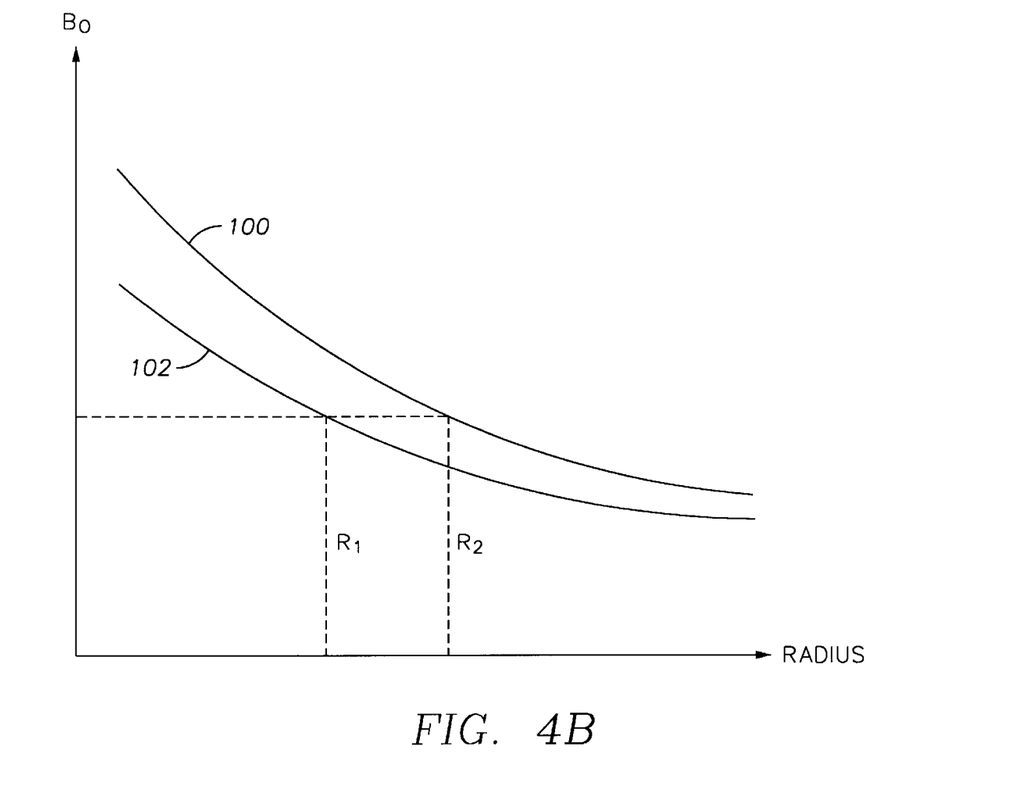
FIG. 4B shows graph of the amplitude distribution of the static magnetic field for the alternative embodiment of FIG. 4A.

FIG. 4A shows an alternative embodiment of the present invention. The embodiment in FIG. 4A can provide phase measurement of the NMR signal with respect to the RF magnetic field at two different radii without changing the frequency of the RF magnetic field. The magnet 62 induces a static magnetic field in the earth formations (26 in FIG. 1) which has a known radial dependence. The radial dependence of the static magnetic field can be changed by including a field control coil 163 connected to a variable DC power source 104. The variable DC source 104 can be controlled by the system operator from the earth's surface or alternatively by the computer (92 in FIG. 3). When DC power is applied to the field control coil 163, an additional static magnetic field is generated, this additional field having a radial dependence equal to $\alpha_2/R^2$. The dependence of the static magnetic field induced by the magnet 62 including the field control coil 163 is shown graphically in FIG. 4B both with DC applied to the field control coil 163 shown as curve 100, and without DC applied, shown as curve 102. By superposition, the total magnitude of the static magnetic field imparted to the earth formations 26 can be expressed as:

$$B_0(R) = \frac{a_1 + a_2}{R^2} \qquad (8)$$

For the RF magnetic field frequency ω the radius of the sensitive volume (58 in FIG. 2) when the DC is applied is related to the static field strength without the DC applied by the expression:

$$\frac{\omega}{\gamma} = \frac{a_1}{R_1^2} = \frac{a_1 + a_2}{R_2^2} \qquad (9)$$

The phase difference measured between signals corresponding to the two different magnitudes of static magnetic field strength can be expressed as: which can be readily solved for the conductivity σ.

It is to be understood that the embodiment described herein including the field $$\Delta\phi = \sqrt{\frac{\mu_0 \omega \sigma}{2}} \cdot (R_1 - R_2) \qquad (10)$$

control coil 163 is meant to serve only as an example of apparatus for measuring the phase at a single frequency but at more than one radius of the sensitive volume by varying the magnitude of the static magnetic field. Another way to vary the static field strength would be to use two separate instruments similar to the one shown in FIG. 2, each instrument having a different strength magnet (62 in FIG. 2). Each magnet (62 in FIG. 2) would therefore have a different magnetic field amplitude distribution, so that the radius of the sensitive volume (58 in FIG. 2) would be different for each instrument, using the same frequency of the RF magnetic field in each apparatus. Accordingly, the embodiment disclosed herein is not to be construed as a limitation on the invention.

Figure 5A:
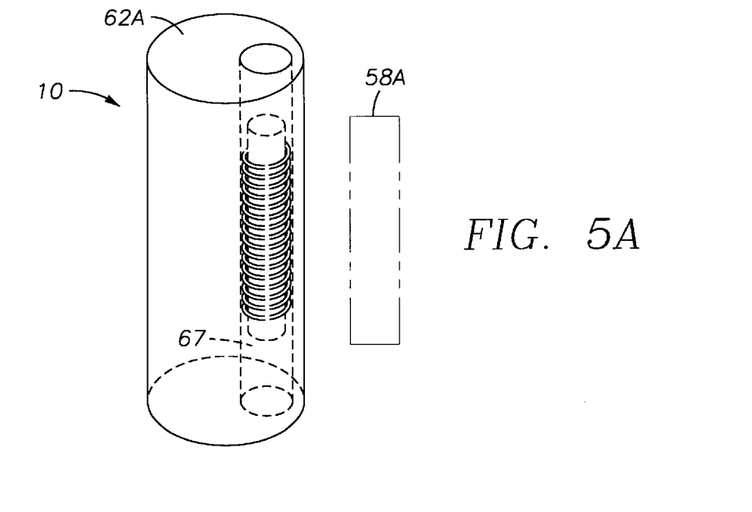
FIG. 5A show another alternative embodiment of the invention.
Figure 5B:
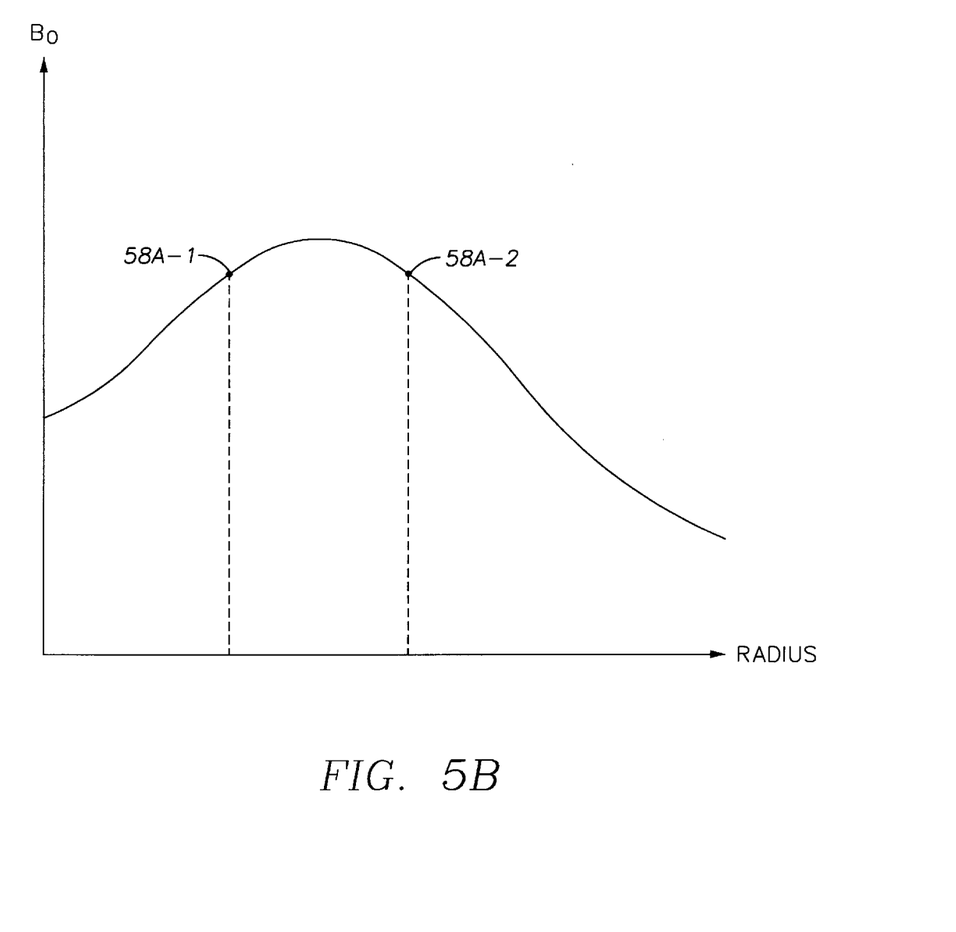
FIG. 5B shows a graph of the amplitude distribution of the static magnetic field for the alternative embodiment of FIG. 5A.

Yet another embodiment of the apparatus is shown in FIG. 5. The magnet 62A of the embodiment shown in FIG. 5 induces a static magnetic field including a region 58A having substantially homogeneous magnetization. The magnet 62A can be similar in construction to the magnet (62 in FIG. 2) of the first embodiment of the invention with the exception that the hole 83A in the magnet 62A of the present embodiment is radially offset towards the edge of the magnet 62A. The radial dependence of the static field induced by the magnet 62A in FIG. 5A is shown graphically in FIG. 5B. The region of homogeneous magnetization shown on the graph of FIG. 5B occurs between radial distances $R_1$ and $R_2$. The amplitude of the RF magnetic field generated by the transceiver antenna 67 in FIG. 5A, however, decreases substantially monotonically with respect to the radial distance from the antenna 67. The RF magnetic field will have a higher amplitude at the edge 58A-1 of the static magnetic field region 58A nearest the instrument 10 (which occurs at $R_1$ on the graph of FIG. 5B), for any constant amplitude RF signal passed through the antenna 67, than it will at the far edge 58A-2 (which occurs at $R_2$ on the graph of FIG. 5B). It is possible to distinguish between the phase of NMR signals received at the near edge 58A-1 from those received from the far edge 58A-2, by adjusting the amount of RF power conducted through the antenna 67 in each RF pulse. For example, if the RF power in a particular pulse is the correct amount to reorient the magnetization of the nuclei in the earth formations (26 in FIG. 1) at the near edge 58A-1 by 180 degrees, the transversal component of the NMR signal from the near edge 58A-1 at will not be detected. Because the RF magnetic field amplitude decreases substantially monotonically with respect to the radius, however, the nuclear magnetic spins will not be reoriented by 180 degrees at the far edge 58A-2 by this particular power level RF pulse. The transversal signal component from the far edge 58A-2 will therefore be detected. In a subsequent RF pulse, the intensity of the RF magnetic field can then be adjusted to cause 180 degree difference in the tilting angle of the nuclear magnetization at the far edge 58A-2, and consequently cause a transversal signal of substantially zero to be detected from the far edge 58A-2. The total NMR signal acquired from this RF pulse will include only transversal signal contributions from the near edge 58A-1. The phases of the signals from the near edge 58A-1 and from the far edge 58A-2 can thus be determined to calculate conductivity as previously described herein. The total power in each of the RF pulses can be properly adjusted by appropriate command signals sent to the pulse programmer (91 in FIG. 3) from the computer (92 in FIG. 3).

Still another embodiment of the invention can provide a measurement of resistivity of the earth formation by measuring amplitudes of the NMR signal. Equation (1) suggests that the conductivity σ can be evaluated from the amplitude of NMR signal. To explain how this is possible, first let the amplitude of the signal S(R) from radius R be expressed as: where C(R) represents a calibration coefficient affected by the receiving antenna coupling factor and the nuclear magnetization at the sensitive volume radius R, and $$S(R) = C(R)\phi \exp\left[-R\frac{\sqrt{\omega\mu_0\sigma}}{2}\right] \qquad (11)$$

φ represents the porosity of the earth formation. By making measurements at two different radii $R_1$ and $R_2$ (assuming operation of the instrument at a single frequency) the ratio of the amplitudes of the signals from the two radii can be expressed as:

$$\frac{S_1(R)}{S_2(R)} = \frac{C_1(R)}{C_2(R)} \exp\left[(R_2 - R_1)\frac{\sqrt{\omega\mu_0\sigma}}{2}\right] \qquad (12)$$

It can be inferred from equation (12) that the signal ratio is not dependent on the formation porosity. Further, the calibration coefficient ratio can be determined as the signal amplitude ratio measured in a nonconductive medium. An example of such a medium could be pure, substantially nonconductive water, or other nonconductive fluid disposed within the pore spaces of a substantially nonconductive rock formation. The conductivity σ can be calculated by solving equation (12).

It is to be understood that other techniques of obtaining the nuclear magnetic resonance signal from various radii may be also used for the method of signal amplitude evaluation of formation conductivity. For example, varying the frequency of the RF magnetic field, varying the power level of the RF magnetic field or varying the amplitude distribution of the static magnetic field as previously described herein could also provide NMR signals from different known radii the amplitude of which NMR signals could be measured and used to determine conductivity of the formation.

3. Combination with Nuclear Magnetic Resonance Measurements

The embodiments of the apparatus disclosed herein are not meant to be limited only to measuring conductivity (resistivity) of the earth formations (26 in FIG. 1) by measuring phase of the NMR signals with respect to the phase of the RF magnetic field. As disclosed herein, each embodiment of the apparatus can also make measurements of the nuclear magnetic resonance properties of the earth formations (26 in FIG. 1), including nuclear spin relaxation time and pulse-echo amplitude decay. As is understood by those skilled in the art, the nuclear magnetic resonance properties can be used to determine petrophysical properties of interest such as fractional volume of pore space (referred to as porosity) in the earth formations (26 in FIG. 1). As is also understood by those skilled in the art, such petrophysical properties of interest can be combined with measurements of resistivity made as disclosed herein in order to infer the native fluid content of the earth formations.

The present invention can be particularly valuable for providing measurements of the resistivity of the earth formations and fractional volume of pore space of the earth formations because these measurements can originate from the same sensitive volume (such as 58 in FIG. 2). Prior art means for determining the resistivity and porosity typically do not measure these properties within the same sensitive volume of the earth formations. Resistivity of the earth formations can vary with radial depth from the wellbore as a liquid phase of the drilling mud (34 in FIG. 1) can be forced into the pore spaces of the earth formation by differential pressure. Forcing the liquid phase of the drilling mud into the pore spaces of the formation displaces native fluid present in these same pore spaces, which can change the resistivity. In order to measure the resistivity of the formation in a sensitive volume substantially unaffected by the fluid displacement, prior art resistivity tools typically measure resistivity within a sensitive volume radially spaced apart from the wellbore. Most prior art porosity devices, however, have sensitive volumes near the wall of the wellbore. As is understood by those skilled in the art, the properties of the earth formation can change with respect to radial depth from the wellbore. The sensitive volume measured by the prior art porosity tools may not correspond to the porosity within the sensitive volume measured by the prior art resistivity tools.

The nuclear magnetic resonance measurements of the present invention used to determine both resistivity and porosity originate from the same sensitive volume, therefore the present invention can provide determination of porosity and resistivity from the same sensitive volume within the earth formation.

It will be readily apparent to those skilled in the art that there are other embodiments of the present invention which do not depart from the spirit of the invention disclosed herein. Therefore the present invention should be limited in scope only by the attached claims.

What is claimed is:

1. An apparatus for determining resistivity of a medium, comprising:

a magnet for inducing a static magnetic field in said medium;

means for generating a radio frequency magnetic field for exciting nuclei in said medium; and means for receiving nuclear magnetic resonance signals from said excited nuclei, said means for receiving including means for measuring a phase of said nuclear magnetic resonance signals with respect to said radio frequency magnetic field, said means for measuring phase including means for calculating said resistivity from said measurement of phase.

2. The apparatus as defined in claim 1 further comprising means for selectively varying a frequency of said radio frequency magnetic field.

3. The apparatus as defined in claim 1 further comprising means for selectively varying an amplitude distribution of said static magnetic field.

4. The apparatus as defined in claim 1 further comprising means for selectively varying an amplitude of said radio frequency magnetic field.

5. The apparatus as defined in claim 1 wherein said medium comprises earth formations penetrated by a wellbore.

6. An apparatus for determining resistivity of materials to be analyzed, comprising:

a magnet for inducing a static magnetic field in a region containing said materials;

means for generating a radio frequency magnetic field in said region for exciting nuclei of said materials;

means for selectively varying a frequency of said radio frequency magnetic field; and means for receiving nuclear magnetic resonance signals from said excited nuclei, said means for receiving including means for measuring a phase of said nuclear magnetic resonance signals with respect to said radio frequency magnetic field, said means for measuring phase including means for calculating said resistivity from said measurement of phase.

7. The apparatus as defied in claim 6 wherein said means for generating comprises a longitudinal dipole antenna.

8. The apparatus as defined in claim 7 wherein said antenna comprises a wire coil wound so that turns of said coil lie in planes substantially perpendicular to a longitudinal axis of said apparatus, said antenna including a high magnetic permeability ferrite disposed inside said coil.

9. The apparatus as defined in claim 8 further comprising means for selectively varying a static magnetic field in said high magnetic permeability ferrite so that a tuning frequency of said means for generating may be selectively varied.

10. The apparatus as defined in claim 9 wherein said means for selectively varying said static magnetic field comprises a frequency control coil wound about said ferrite and a selectively operable DC power source connected to said frequency control coil.

11. An apparatus for determining resistivity of materials to be analyzed, comprising:

a first magnet for inducing a static magnetic field in a region containing said materials;

means for generating a radio frequency magnetic field in said region for exciting nuclei of said materials;

means for selectively varying an amplitude distribution of said static magnetic field; and means for receiving nuclear magnetic resonance signals from said excited nuclei, said means for receiving including means for measuring a phase of said resonance signal with respect to said radio frequency magnetic field, said means for measuring phase including means for calculating said resistivity from said measurement of phase.

12. The apparatus as defined in claim 11 wherein said means for selectively varying said amplitude distribution includes a field control coil wound around said magnet and a selectively controllable DC power source connected to said field control coil.

13. The apparatus as defined in claim 11 wherein said means for selectively varying said amplitude distribution comprises a second magnet having a different magnetic field amplitude distribution than said first magnet, said apparatus further comprising an additional means for generating and an additional means for receiving disposed proximal to said second magnet.

14. An apparatus for determining resistivity of materials to be analyzed, comprising:
   a magnet for generating a static magnetic field in said materials to be analyzed, said static magnetic field including at least two locations having substantially equal amplitude;
   means for generating a radio frequency magnetic field in said materials, said means for generating including means for selectively controlling power of said radio frequency magnetic field so that nuclear excitation occurs at said at least two locations within said region, said excitation having predetermined difference in amplitude between said locations; and
   means for receiving nuclear magnetic resonance signals from excited nuclei within said region, said means for receiving including means for measuring a difference in phase between said magnetic resonance signals and said radio frequency magnetic field, said means for receiving including means for providing an output indicative of resistivity of said materials.

15. A method for determining resistivity of a medium, comprising:
   inducing a first static magnetic field in said medium;
   generating a radio frequency magnetic field at a first frequency in said medium so as to excite nuclei of said medium,
   receiving nuclear magnetic resonance signals from said excited nuclei at said first frequency;
   measuring a difference in phase between said resonance signals and said radio frequency magnetic field; and
   calculating said resistivity from said difference in phase.

16. The method as defined in claim 15 further comprising:
   generating said radio frequency magnetic field at a second frequency to excite said nuclei;
   receiving nuclear magnetic resonance signals at said second frequency;
   measuring a difference in phase between said radio frequency magnetic field and said nuclear magnetic resonance signals at said second frequency;
   calculating said resistivity by combining said measurement of phase difference at said first frequency with said measurement of phase difference at said second frequency.

17. The method as defined in claim 15 further comprising:
   varying an amplitude distribution of said static magnetic field;
   repeating said step of generating said radio frequency magnetic field;
   repeating said step of receiving said nuclear magnetic resonance signals;
   repeating said step of measuring said difference in phase;
   calculating said resistivity by combining said measurement of difference in phase from prior to said step of varying said amplitude distribution with said measurement of difference in phase from after said step of varying said amplitude distribution.

18. The method as defined in claim 17 wherein said step of varying said static magnetic field comprises superposing a selectively controllable magnetic field onto said static magnetic field.

19. The method as defined in claim 17 wherein said step of varying said static magnetic field comprises inducing a second static magnetic field in said medium, said second static magnetic field having different amplitude distribution than said first static magnetic field.

20. The method as defined in claim 15 further comprising:
   generating said radio frequency magnetic field so that said radio frequency magnetic field has a power selected to induce a predetermined amplitude difference in said nuclear magnetic resonance signals between at least two predetermined positions within said medium;
   measuring said nuclear magnetic resonance signals induced in said medium;
   measuring at each of said predetermined positions a phase shift between said nuclear magnetic resonance signals and said radio frequency magnetic field; and
   calculating said resistivity from said measurements of phase shift.

21. A method for determining resistivity of a medium, comprising:
   inducing a static magnetic field in said medium;
   generating a radio frequency magnetic field in said medium at a first frequency so as to excite nuclei of said medium,
   receiving nuclear magnetic resonance signals at said first frequency;
   generating said radio frequency magnetic field in said medium at a second frequency;
   receiving said nuclear magnetic resonance signals at said second frequency;
   measuring a difference in phase shift with respect to a predetermined reference between said resonance signals measured at said first frequency and said resonance signals measured at said second frequency; and
   calculating said resistivity from said difference in phase.

22. The method as defined in claim 21 further comprising:
   repeating said steps of generating and receiving at a plurality of different first frequencies;
   repeating said steps of generating and receiving at a plurality of different second frequencies; and
   calculating differences in phase, and resistivity corresponding thereto, for a plurality of different sensitive volumes each of said sensitive volumes having a different radial separation from a central axis, each of said radial separations corresponding to one of said plurality of different first and second frequencies.

23. The method as defined in claim 21 wherein said steps of generating and said steps of receiving at different frequencies are performed by selectively controlling a static magnetic field amplitude in a high magnetic permeability ferrite disposed within an antenna used to perform said steps of generating and said steps of receiving.

24. A method for determining resistivity of earth formations penetrated by a wellbore, comprising:

inducing a first static magnetic field in said earth formations;

generating a radio frequency magnetic field in said earth formations to excite nuclei of said earth formations at a first radial depth from said wellbore;

receiving nuclear magnetic resonance signals from said excited nuclei;

selectively varying an amplitude distribution of said static magnetic field;

repeating said step of generating said radio frequency magnetic field;

repeating said step of receiving said nuclear magnetic resonance signals;

measuring a difference in phase between said resonance signals measured in said step of receiving performed prior to said step of varying said amplitude distribution and said step of receiving performed after said step of varying; and calculating said resistivity of said earth formations from said difference in phase.

25. The method as defined in claim 24 wherein said step of varying said amplitude distribution comprises superposing a controllable static magnetic field upon said static magnetic field induced during said step of inducing.

26. The method as defined in claim 24 wherein said step of selectively varying said amplitude distribution includes inducing a second static magnetic field having a different amplitude distribution than said first static magnetic field.

27. A method of determining resistivity of an earth formation, comprising:

inducing a static magnetic field in said earth formation, said static magnetic field comprising at least two regions having substantially the same amplitude;

generating a radio frequency magnetic field in said earth formation, said radio frequency magnetic field having an amplitude distribution selected to excite nuclei in said earth formation to generate nuclear magnetic resonance signals having a predetermined amplitude difference between said at least two regions;

measuring nuclear magnetic resonance signals induced in said earth formation;

measuring at each of said at least two regions a phase shift between said nuclear magnetic resonance signals and said radio frequency magnetic field; and calculating said resistivity from said measurements of phase shift.

28. An apparatus for determining resistivity and porosity from a region within materials to be analyzed, comprising:

a magnet for inducing a static magnetic field in said region containing said materials;

means for generating a radio frequency magnetic field in said region for exciting nuclei of said materials; and means for receiving nuclear magnetic resonance signals from said excited nuclei, said means for receiving including means for measuring a phase of said nuclear magnetic resonance signals with respect to said radio frequency magnetic field, said means for receiving including means for measuring an amplitude of said resonance signals, said means for receiving providing an output indicative of said resistivity and said porosity within said region.

29. The apparatus as defined in claim 28 further comprising a means for selectively varying a frequency of said radio frequency magnetic field.

30. The apparatus as defined in claim 28 further comprising means for selectively varying an amplitude distribution of said static magnetic field.

31. The apparatus as defined in claim 28 further comprising means for selectively varying an amplitude of said radio frequency magnetic field.

32. A method for determining resistivity and porosity within a selected volume of earth formations penetrated by a wellbore, comprising:

inducing a static magnetic field in said earth formations;

generating a radio frequency magnetic field in said earth formations at a first frequency so as to excite nuclei of said earth formations at a first radial depth from said wellbore;

receiving nuclear magnetic resonance signals at said first frequency;

generating said radio frequency magnetic field in said earth formations at a second frequency so as to excite nuclei of said earth formations at a second radial depth from said wellbore;

receiving said nuclear magnetic resonance signals at said second frequency;

measuring amplitude of said nuclear magnetic resonance signals at said first frequency and at said second frequency;

measuring a difference in phase shift with respect to a predetermined reference between said resonance signals measured at said first frequency and said resonance signals measured at said second frequency;

calculating said resistivity of said earth formations from said difference in phase; and calculating said porosity from said amplitude.

33. The method as defined in claim 32 wherein said steps of generating and said steps of receiving at said first and second frequencies are performed by selectively controlling a tuning frequency of an antenna used to perform said steps of generating and said steps of receiving.

34. A method of determining resistivity and porosity of an earth formation, comprising:

inducing a static magnetic field in said earth formation, said static magnetic field comprising a region having substantially homogeneous magnetic field amplitude;

generating a radio frequency magnetic field in said earth formation, said radio frequency magnetic field having an amplitude distribution selected to excite nuclei in said earth formation having a predetermined phase shift between at least two predetermined positions within said region;

measuring nuclear magnetic resonance signals induced in said earth formation;

measuring amplitude of said nuclear magnetic resonance signals;

measuring at each of said predetermined positions a phase shift between said nuclear magnetic resonance signals and said radio frequency magnetic field;

calculating said resistivity from said measurements of phase shift; and calculating said porosity from said measurements of amplitude.

35. A method for determining resistivity and porosity of earth formations penetrated by a wellbore, comprising:

inducing a first static magnetic field in said earth formations;

generating a radio frequency magnetic field in said earth formations to excite nuclei of said earth formations at a first radial depth from said wellbore;

receiving nuclear magnetic resonance signals from said excited nuclei;

selectively varying an amplitude distribution of said static magnetic field;

repeating said step of generating said radio frequency magnetic field;

repeating said step of receiving said nuclear magnetic resonance signals;

measuring amplitude of said nuclear magnetic resonance signals;

measuring a difference in phase shift with respect to a predetermined reference between said resonance signals measured in said step of receiving prior to said step of varying and said amplitude distribution and said step of receiving after said step of varying said amplitude distribution;

calculating said resistivity of said earth formations from said difference in phase; and calculating said porosity of said earth formations from said amplitude.

36. The method as defined in claim 35 wherein said step of varying said amplitude distribution comprises superposing a controllable static magnetic field upon said static field induced during said step of inducing.

37. The method as defined in claim 35 wherein said step of selectively varying said amplitude distribution includes inducing a second static magnetic field having a different amplitude distribution than said first static magnetic field.

38. An apparatus for determining resistivity of materials to be analyzed, comprising:

a magnet for inducing a static magnetic field in a region containing said materials;

means for generating a radio frequency magnetic field in said region for exciting nuclei of said materials, said means for generating comprising a longitudinal dipole antenna and a transversal dipole antenna; and means for receiving nuclear magnetic resonance signals from said excited nuclei, said means for receiving including means for measuring a phase of said nuclear magnetic resonance signals with respect to said radio frequency magnetic field, said means for measuring phase including means for calculating said resistivity from said measurement of phase, said means for receiving comprising a longitudinal dipole antenna and a transversal dipole antenna, whereby said resistivity can be determined along substantially orthogonal directions.

39. The apparatus as defined in claim 38 further comprising a means for selectively varying a frequency of said radio frequency magnetic field.

40. The apparatus as defined in claim 38 further comprising a means for varying an amplitude distribution of said static magnetic field.

41. The apparatus as defined in claim 38 further comprising a means for selectively varying an amplitude of said radio frequency magnetic field.

42. A method of determining resistivity of a medium, comprising:

inducing a static magnetic field in said medium;

generating a radio frequency magnetic field in said medium so as to excite nuclei of said medium, said radio frequency magnetic field having a first electric field component orientation;

receiving nuclear magnetic resonance signals from said excited nuclei, said step of receiving performed so as to be sensitive to said first electric field component orientation;

measuring a difference in phase between said resonance signals and said radio frequency magnetic field; and calculating said resistivity from said difference in phase.

43. The method as defined in claim 42 further comprising:

repeating said steps of generating, receiving, measuring and calculating, wherein repeating said step of generating includes said radio frequency magnetic field having a second electric field component orientation substantially orthogonal to said first electric field component orientation; and wherein repeating said step of receiving is performed so as to be sensitive to said second electric field component orientation, so that said resistivity can be determined along two substantially orthogonal directions.

44. The method as defined in claim 43 further comprising:

generating said radio frequency magnetic field at a second frequency to excite said nuclei;

receiving nuclear magnetic resonance signals at said second frequency;

measuring a difference in phase between said radio frequency magnetic field and said nuclear magnetic resonance signals at said second frequency;

calculating said resistivity by combining said measurement of phase difference at said first frequency with said measurement of phase difference at said second frequency.

45. The method as defined in claim 43 further comprising:

varying an amplitude distribution of said static magnetic field;

repeating said step of generating said radio frequency magnetic field;

repeating said step of receiving said nuclear magnetic resonance signals;

repeating said step of measuring said difference in phase;

calculating said resistivity by combining said measurement of difference in phase from prior to said step of varying said amplitude distribution with said measurement of difference in phase from after said step of varying said amplitude distribution.

46. The method as defined in claim 45 wherein said step of varying said static magnetic field comprises superposing a selectively controllable magnetic field onto said static magnetic field.

47. The method as defined in claim 45 wherein said step of varying said static magnetic field comprises inducing a second static magnetic field in said medium, said second static magnetic field having different amplitude distribution than said first static magnetic field.

48. The method as defined in claim 45 further comprising:

generating said radio frequency magnetic field so as to have a power selected to induce a predetermined amplitude difference in nuclear magnetic resonance signals between at least two predetermined positions within said medium;

measuring nuclear magnetic resonance signals induced in said medium;

measuring at each of said predetermined positions a phase shift between said nuclear magnetic resonance signals and said radio frequency magnetic field; and calculating said resistivity from said measurements of phase shift.

49. An apparatus for determining resistivity of materials to be analyzed, comprising:
   a magnet for inducing a static magnetic field in said materials;
   means for generating a radio frequency magnetic field for exciting nuclei of said materials; and
   means for receiving nuclear magnetic resonance signals from said excited nuclei, said means for receiving including means for measuring an amplitude of said resonance signals, said means for measuring amplitude including means for calculating said resistivity from measurements of said amplitude.

50. The apparatus as defined in claim 49 further comprising a means for selectively varying a frequency of said radio frequency magnetic field.

51. The apparatus as defined in claim 49 further comprising means for selectively varying an amplitude distribution of said static magnetic field.

52. The apparatus as defined in claim 49 further comprising means for selectively varying power of said radio frequency magnetic field.

53. A method for determining resistivity of a medium, comprising:
   inducing a first static magnetic field in said medium;
   generating a radio frequency magnetic field at a first frequency in said medium so as to excite nuclei of said medium at a first radial depth in said medium;
   receiving nuclear magnetic resonance signals from said excited nuclei at said first radial depth;
   measuring an amplitude of said resonance signals from said first radial depth;
   generating a radio frequency magnetic field so as to excite nuclei at a second radial depth within said medium;
   receiving nuclear magnetic resonance signals from said excited nuclei at second radial depth;
   measuring an amplitude of said resonance signals from said second radial depth; and
   calculating said resistivity from a difference between said amplitude measured from said excited nuclei at said first radial depth and said amplitude measured from said excited nuclei at said second radial depth.

54. The method as defined in claim 53 wherein said step of generating said radio frequency magnetic field so as to excite nuclei at said second radial depth comprises generating said radio frequency magnetic field at a second frequency to excite said nuclei and receiving said nuclear magnetic resonance signals at said second frequency.

55. The method as defined in claim 53 wherein said step of generating said radio frequency magnetic field so as to excite nuclei at said second radial depth comprises varying an amplitude distribution of said static magnetic field; and repeating said step of generating said radio frequency magnetic field.

56. The method as defined in claim 55 wherein varying said amplitude distribution of said static magnetic field comprises superposing a selectively controllable magnetic field onto said static magnetic field.

57. The method as defined in claim 55 wherein varying said static magnetic field comprises inducing a second static magnetic field in said medium, said second static magnetic field having different amplitude distribution than said first static magnetic field.

58. The method as defined in claim 53 wherein said step of generating said radio frequency magnetic field so as to excite nuclei at said second radial depth comprises generating said radio frequency magnetic field so as to have a power selected to induce a predetermined amplitude difference in said nuclear magnetic resonance signals between at least two predetermined positions within said medium; and measuring said nuclear magnetic resonance signals induced in said medium.

* * * * *